(12) United States Patent
Zielinski

(10) Patent No.: US 7,909,875 B2
(45) Date of Patent: *Mar. 22, 2011

(54) ARTIFICIAL SPINAL DISK

(76) Inventor: Steven C. Zielinski, McGregor, TX (US)

( * ) Notice: Subject to any disclaimer, the term of this patent is extended or adjusted under 35 U.S.C. 154(b) by 150 days.

This patent is subject to a terminal disclaimer.

(21) Appl. No.: 12/359,962

(22) Filed: Jan. 26, 2009

(65) Prior Publication Data

US 2009/0192618 A1 Jul. 30, 2009

Related U.S. Application Data

(63) Continuation-in-part of application No. 12/022,947, filed on Jan. 30, 2008.

(51) Int. Cl.
*A61F 2/44* (2006.01)
(52) U.S. Cl. .................................... 623/17.11
(58) Field of Classification Search .... 623/17.11–17.16; 606/280, 287
See application file for complete search history.

(56) References Cited

U.S. PATENT DOCUMENTS

| | | | |
|---|---|---|---|
| 4,611,581 A | 9/1986 | Steffee | |
| 4,759,766 A | 7/1988 | Buttner-Janz et al. | |
| 5,180,381 A | 1/1993 | Aust et al. | |
| 5,324,290 A | 6/1994 | Zdeblick et al. | |
| 5,401,269 A | 3/1995 | Buttner-Janz et al. | |
| 5,556,431 A | 9/1996 | Buttner-Janz et al. | |
| 5,683,465 A | 11/1997 | Shinn et al. | |
| 5,772,661 A | 6/1998 | Michelson | |
| 6,248,106 B1 | 6/2001 | Ferree | |
| 6,461,359 B1 | 10/2002 | Tribus et al. | |
| 6,764,489 B2 | 7/2004 | Ferree | |
| 6,764,491 B2 | 7/2004 | Frey et al. | |
| 6,830,570 B1 | 12/2004 | Frey et al. | |
| 6,923,814 B1 | 8/2005 | Hildebrand et al. | |
| 7,195,644 B2 | 3/2007 | Diaz et al. | |
| 7,214,244 B2 | 5/2007 | Zubok et al. | |
| 7,235,101 B2 | 6/2007 | Berry et al. | |
| 7,282,065 B2 | 10/2007 | Kirschman | |
| 2002/0091390 A1 | 7/2002 | Michelson | |
| 2003/0158553 A1 | 8/2003 | Michelson | |
| 2003/0187441 A1 | 10/2003 | Bolger et al. | |
| 2003/0208203 A1 | 11/2003 | Lim et al. | |
| 2004/0030346 A1 | 2/2004 | Frey et al. | |
| 2004/0092929 A1 | 5/2004 | Zindrick | |
| 2004/0225290 A1 | 11/2004 | Ferree | |
| 2006/0089644 A1 | 4/2006 | Felix | |

(Continued)

FOREIGN PATENT DOCUMENTS

EP 1488755 12/2004

(Continued)

OTHER PUBLICATIONS

Non Final Office Action, U.S. Appl. No. 11/363,607, pp. 1-18.

(Continued)

*Primary Examiner* — Eduardo C Robert
*Assistant Examiner* — Summer L Kostelnik
(74) *Attorney, Agent, or Firm* — Samuel M. Freund; Cochran Freund & Young LLC

(57) ABSTRACT

An artificial spinal implant for placement between adjacent vertebrae to replace disk material and to stabilize the involved vertebrae is described. The artificial disk may be disassembled for installation and/or removal for repair, replacement or adjustment, and may be assembled from the front of the spine as individual component parts, thereby permitting alignment of the spine during the assembly process, and the stabilization of the involved vertebrae once assembly has been completed. Further, the components may be chosen from a set of similar components having different sizes, thereby enabling the implant to be tailor fit to the requirements of the patient.

24 Claims, 8 Drawing Sheets

U.S. PATENT DOCUMENTS

| | | |
|---|---|---|
| 2006/0190084 A1 | 8/2006 | Doubler et al. |
| 2006/0241600 A1 | 10/2006 | Ensign et al. |
| 2006/0293670 A1 | 12/2006 | Smisson, III et al. |
| 2007/0162133 A1 | 7/2007 | Doubler et al. |
| 2007/0173842 A1 | 7/2007 | Abdou |
| 2008/0015704 A1 | 1/2008 | Gradl et al. |

FOREIGN PATENT DOCUMENTS

| | | |
|---|---|---|
| WO | 9627321 | 9/1996 |
| WO | 9841160 A1 | 9/1998 |
| WO | 0101874 | 1/2001 |

OTHER PUBLICATIONS

Non Final Office Action, U.S. Appl. No. 12/022,947, pp. 1-26.
International Search Report for PCT/US09/32157, International Searching Authority, Mar. 27, 2009, pp. 1-12.
Non-Final Office Action dated Jul. 9, 2008, U.S. Appl. No. 11/363,607, pp. 1-9.
Non-Final Office Action dated Nov. 14, 2008, U.S. Appl. No. 11/363,607, pp. 1-11.
Final Office Action dated May 26, 2009, U.S. Appl. No. 11/363,607, pp. 1-13.
Final Office Action, U.S. Appl. No. 11/363,607, pp. 1-12.

ARTIFICIAL SPINAL DISK

RELATED CASES

The present patent application is a continuation-in-part patent application of copending U.S. patent application Ser. No. 12/022,947 for "ARTIFICIAL SPINAL DISK" by Steven C. Zielinski which was filed on Jan. 30, 2008, the disclosure and teachings of which are hereby incorporated by reference herein.

FIELD OF THE INVENTION

The present invention relates generally to orthopedic surgery and, more particularly, to artificial spinal implants for insertion between spinal vertebrae which may be used to replace ruptured or excised spinal disks and to stabilize the spine.

BACKGROUND OF THE INVENTION

It is known that spinal musculature does little to stabilize facet joint articulation in the spine. This function is provided by the ligament structure. Most artificial disk replacements today are for degenerate disks which are causing pain. The bone, muscle and the ligaments are all intact, and the spine itself is stable. When a spine is unstable and the bones and ligaments allow the spine to move out of alignment, rods and screws are used to provide stability. In some situations a spinal fusion is performed.

Spinal prostheses for replacement of missing or excised disk material that replicate the functions of the missing tissue have been sought. The CHARITÉ® Artificial Disc was developed at the CHARITÉ University Hospital in Berlin, Germany in the mid-1980s. Further refinements to the design were incorporated with the cooperation of the staff at Waldemar Link GmbH. The basic device includes a sliding core made from a medical grade plastic, sandwiched between two metal endplates made from medical grade cobalt chromium alloy. The endplates support the core and have small teeth which secure them to the vertebrae above and below the disk space. In a clinical study, patients were observed to have motion between 0° and 21° while bending forward and backward. U.S. Pat. No. 4,759,766 for "Intervertebral Disc Endoprosthesis" which issued to Karin Büttner-Janz et al. on Jul. 26, 1988; U.S. Pat. No. 5,401,269 for "Intervertebral Disc Endoprosthesis" which issued to Karin Büttner-Janz et al. on Mar. 28, 1995; and U.S. Pat. No. 5,556,431 for "Intervertebral Disc Endoprosthesis" which issued to Karin Büttner-Janz on Sep. 17, 1996 represent several embodiments of this disk.

U.S. Pat. No. 5,683,465 for "Artificial Intervertebral Disk Prosthesis" which issued to Gary Lee Shinn et al. on Nov. 4, 1997 includes a first disk half having a portion of a socket attached to a first plate, a second disk half having a portion of a ball attached to a second plate, the socket further having a plurality of expansion slots which expand to allow the portion of a ball to be inserted into the socket such that the expansion slots expand around the portion of a ball to be inserted into the socket and then contract to retain the portion of a ball therein. The disk is fastened to the vertebrae by pins, tabs or by a first annulus or second annulus, each of which extend from the disk. A flexible substantially toroidal enclosure is attached to the perimeter of the first plate and to the perimeter of the second plate when desired to form a barrier between the disk and any proximal organic material.

U.S. Pat. No. 7,195,644 for "Ball And Dual Socket Joint" which issued to Robert Diaz et al. on Mar. 27, 2007, U.S. Patent Application Publication 2006/0190084 (Aug. 24, 2006) for "Interior Insert Ball And Dual Socket Joint" by Robert Doubler et al., and U.S. Patent Publication No. 2007/0162133 (Jul. 12, 2007) by Robert Doubler et al. teach a spinal implant inserted between adjacent vertebrae to function as a disk prosthesis which includes two plates fastened to adjacent vertebrae facing each other, the facing sides of the plates each having a depending skirt formed as concentric arcs and bowed or tapered in the axial direction. Depressions are centrally located between the arcs of the plates and a ceramic ball is universally movable in the depressions.

U.S. Pat. No. 7,282,065 for "Disk Augmentation System And Method" which issued to David Louis Kirschman on Oct. 16, 2007 describes a retainer including artificial supports posterior to or exterior of a spinal column and a spinal column axis for receiving and securing at least one artificial compression body in a supported relationship to facilitate reducing the load on one or more natural disks of a patient.

With the exceptions of the '065 and the '644 patents, the above patents and patent applications provide no stability to the spine in the situation where stability is not provided by existing ligaments. The '065 patent does not permit significant movement of the vertebrae involved. The '644 patent teaches that the facing sides of the plates each have a depending skirt formed as concentric depending and upstanding arcs of about 90 degrees, such that each interrupted skirt may be oriented whereby depending opposed arcs are aligned with upstanding opposed arcs, thereby interlocking the plates in a movable joint that cannot be separated axially. The contacting surfaces are spherical or bowed from the plate at least to the height of the diameter of the ball. This design does not permit lateral movement between the plates.

SUMMARY OF THE INVENTION

Accordingly, it is an object of the present invention to provide an artificial spinal disk for stabilizing spinal vertebrae.

Another object of the invention is to provide an artificial spinal disk for stabilizing spinal vertebrae while permitting significant motion of the stabilized vertebrae.

Still another object of the invention is to provide an artificial spinal disk for stabilizing spinal vertebrae while permitting significant motion of the stabilized vertebrae in situations where there is little muscle, ligament or bone structure to support the vertebrae.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the artificial spinal disk for placement between adjacent spinal vertebrae to replace disk material, hereof, includes in combination: a first flat plate for attaching to the endplate of a first vertebral body the first flat plate having a first surface and an opposing second surface, a front wall, and a slot opening through the second surface and through the front wall; a second flat plate having a first surface and an opposing second surface, adapted to slide into the slot in the first plate; a post having a first end, and a second end perpendicularly attached to the second surface of the second plate and extending through the slot opening in the second surface of the first plate; a ball having a portion of the spherical surface thereof transitioned into a conical portion, wherein the smaller end of the conical portion is mounted on the first end of the post; means for rigidly affixing the second plate to the first plate; a third flat plate for attaching to the endplate of a second vertebral body, the endplate of the second vertebral body opposing the endplate of the first vertebral body, the third flat plate having a first surface and an opposing second surface, a front wall, and a slot opening through the second flat surface and through the front wall; a fourth member having a first surface, an opposing second surface and a front wall, and adapted to slide into the slot in the third plate, the fourth member having a slot therein opening through the second surface and through the front wall thereof and a first channel within the slot opening through the front wall of the fourth member adapted to slidably and rotatably receive the ball; means for rigidly affixing the fourth member to the third plate; a fifth member having a first surface, an opposing second surface, and a rear wall, and adapted to slide into the slot in the fourth member, the second surface having a second channel therein adapted to slidably and rotatably receive the ball and the post, and opening through the rear wall; and means for rigidly affixing the fifth member to the fourth member, whereby the channel in the fifth member and the channel in the fourth member are opposing, parallel channels wherein the ball may rotate and slide a chosen distance therein.

In another aspect of the invention and in accordance with its objects and purposes, the artificial spinal disk for placement between adjacent spinal vertebrae to replace disk material, hereof, includes in combination: a first flat plate for attaching to the endplate of a first vertebral body, the first flat plate having a first surface and an opposing second surface, a front wall, and a slot opening through the second surface and through the front wall; a second flat plate having a first surface and an opposing second surface, and adapted to slide into the slot in the first plate; a post having a first end, and a second end perpendicularly attached to the second surface of the second plate and extending through the slot opening in the second flat surface of the first plate; a ball having a portion of the spherical surface thereof transitioned into a conical portion, wherein the smaller end of the conical portion is mounted on the first end of the post; means for rigidly affixing the second plate to the first plate; a third member having a first surface, an opposing second surface, and a front wall, the first surface being adapted to be attached to the endplate of a second vertebral body opposing the endplate of the first vertebral body, the third member having a slot therein opening through the second surface and through the front wall thereof and a first channel within the slot opening through the front wall of the third member adapted to slidably and rotatably receive the ball; a fourth member having a first surface, a second opposing surface, and a rear wall, and adapted to slide into the slot in the third member, the second surface having a second channel therein adapted to slidably and rotatably receive the ball, and opening through the rear wall; and means for rigidly affixing the fourth member to the third member, whereby the channel in the third member and the channel in the fourth member form opposing, parallel channels, wherein the ball may rotate and slide a chosen distance therein.

In yet another aspect of the invention and in accordance with its objects and purposes, the artificial spinal disk for placement between adjacent spinal vertebrae to replace disk material, hereof, includes in combination: a first flat plate for attaching to the endplate of a first vertebral body the first flat plate having a first surface and an opposing second surface; a post having a first end, and a second end perpendicularly attached to the second surface of the first plate; a ball having a portion of the spherical surface thereof transitioned into a conical portion, wherein the smaller end of the conical portion is mounted on the first end of the post; a second flat plate for attaching to the endplate of a second vertebral body the endplate of the second vertebral body opposing the endplate of the first vertebral body, the second flat plate having a first surface and an opposing second surface, a front wall, and a slot opening through the second surface and through the front wall; a third member having a first surface, an opposing second surface and a front wall, and adapted to slide into the slot in the second plate, the third member having a slot therein opening through the second surface and through the front wall thereof and a first channel within the slot opening through the front wall of the third member adapted to slidably and rotatably receive the ball; means for rigidly affixing the third member to the second plate; a fourth member having a first surface, an opposing second surface, a rear wall, and adapted to slide into the slot in the third member, the second surface having a second channel therein adapted to slidably and rotatably receive the ball, and opening through the rear wall; and means for rigidly affixing the third member to the fourth member, whereby the channel in the third member and the channel in the fourth member are opposing, parallel channels, wherein the ball may rotate and slide a chosen distance therein.

In still another aspect of the invention and in accordance with its objects and purposes, the artificial spinal disk for placement between adjacent spinal vertebrae to replace disk material, hereof, includes in combination: a first flat plate for attaching to the endplate of a first vertebral body the first flat plate having a first surface and an opposing second surface; a post having a first end, and a second end perpendicularly attached to the second surface of the first plate; a ball having a portion of the spherical surface thereof transitioned into a conical portion, wherein the smaller end of the conical portion is mounted on the first end of the post; a second member having a first surface, an opposing second surface, and a front wall, the first surface adapted to be attached to the endplate of a second vertebral body opposing the endplate of the first vertebral body, the second member having a slot therein opening through the second surface and through the front wall thereof and a first channel within the slot opening through the front wall of the second member adapted to slidably and rotatably receive the ball; a third member having a first surface, an opposing second surface, and a rear wall, and adapted to slide into the slot in the second member, the second surface having a second channel therein adapted to slidably and rotatably receive the ball, and opening through the rear wall; and means for rigidly affixing the third member to the second member, whereby the channel in the second member and the channel in the third member form opposing, parallel channels wherein the ball may rotate and slide a chosen distance therein.

Benefits and advantages of the present invention include, but are not limited to, providing an artificial spinal disk for insertion between two adjacent spinal vertebrae, portions of which may be removed for repair or replacement without damaging the spinal vertebrae. Additionally the spinal implant hereof may be assembled from the front of the spine as individual component parts, thereby permitting alignment of the spine during the assembly process, and the stabilization of the involved vertebrae once assembly has been completed. Further, the components may be chosen from a set of similar components having different sizes, thereby enabling the implant to be tailor fit to the requirements of the patient.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 8A is a schematic representation of another embodiment of the ball mounted to the second plate through a post and described in FIG. 1, hereof, wherein the spherical portion of the ball is transitioned into a conical portion, the smaller end of the conical portion being mounted on the first end of the post, while

DETAILED DESCRIPTION OF THE INVENTION

Briefly, the present invention includes an artificial spinal implant for placement between adjacent vertebrae to replace disk material and stabilize vertebrae involved. The component parts of the implant may be assembled in the space between the vertebrae during surgery as individual components which permits each implant to be tailored to the requirements of the patient. This also permits the spine to be aligned during assembly of the components, the involved vertebrae being stabilized when the assembly is complete. The assembled implant allows controlled anterior/posterior motion of the vertebrae as well as relative rotation thereof and bending therebetween.

Figure 1:
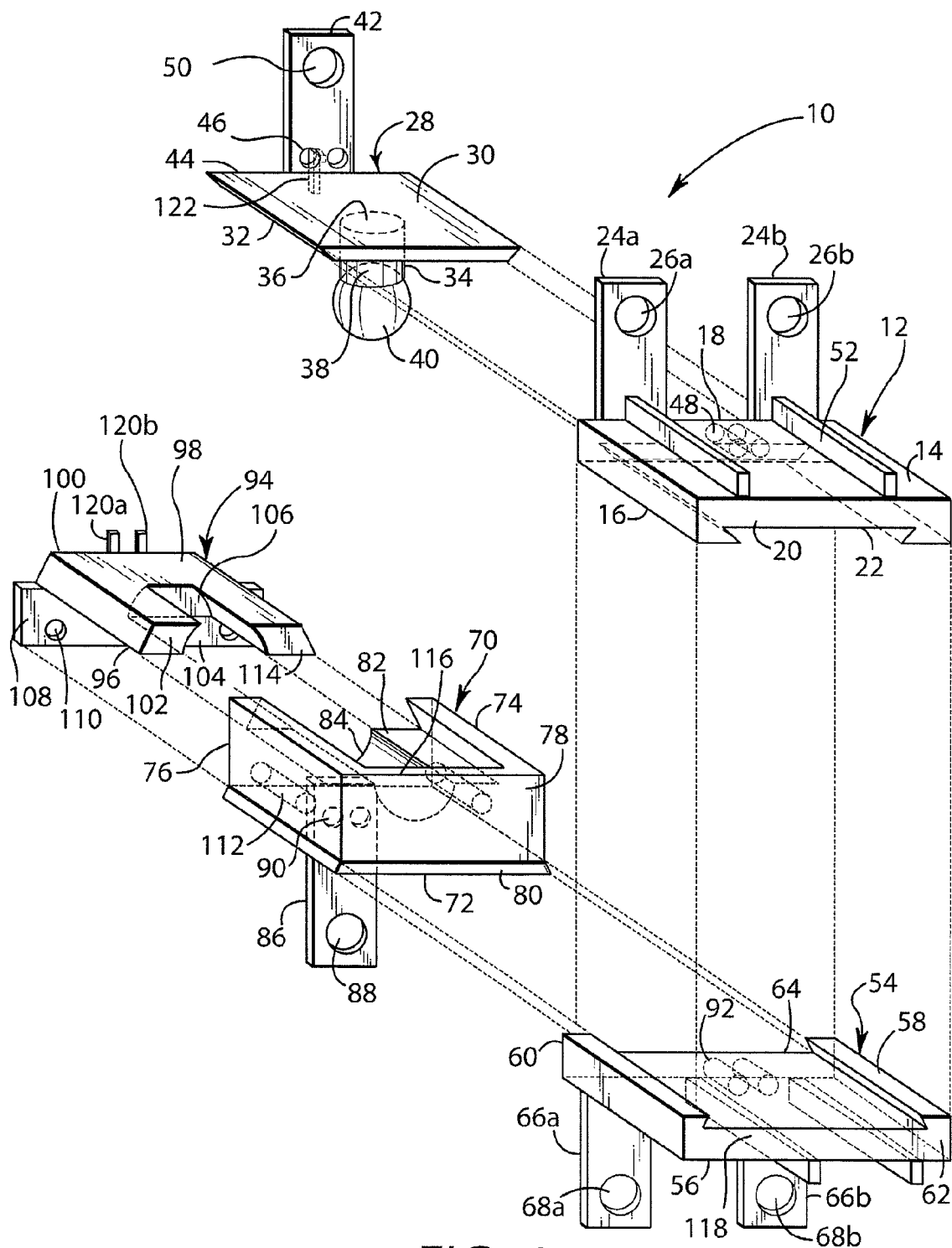
FIG. 1 is a schematic representation of an exploded perspective view of one embodiment of the artificial spine implant of the present invention illustrating first and third flat plates adapted to attach to opposing vertebral bodies; a second plate to which a post having a ball mounted thereon may be attached, the second plate being reversibly received by the first plate; and two members when combined forming a channel for slidably and rotatably restraining the ball and post, one of the two members being reversibly received by the third plate.

Reference will now be made in detail to the present embodiments of the invention, examples of which are illustrated in the accompanying drawings. In the Figures, similar structure will be identified using identical reference characters. Turning now to FIG. 1, a schematic representation of an exploded view of one embodiment of the artificial spine implant, 10, hereof is shown. First flat plate, 12, adapted for attachment to the endplate of a first vertebral body may have first flat surface, 14, second flat surface, 16, parallel thereto, front wall, 18, and rear wall, 20, slot, 22, opening through second flat surface 16 and at least through front surface 16, and means, 24, for attaching plate 12 to the first vertebral body. Beneficially, one example of slot 22 may have a dovetail cross section. However, in what follows, hereinbelow, slots such as slot 22 may have other shapes; rectangular, as an example. One example of attaching means 24 is illustrated as tabs, 24a and 24b, having screw holes, 26a and 26b, therein each adapted for receiving a screw body therethrough effective for affixing plate 12 to the front side of the first vertebral body.

Second flat plate, 28, having first flat surface, 30, and second flat surface, 32, parallel thereto, is adapted to slide into dovetail slot 22 in first plate 12. Post, 34, having first wall, 36, and second wall, 38, is perpendicularly attached to second surface 32 of second plate 28 and extends through the opening of slot 22 in second surface 16 of first plate 12. Ball, 40, is attached to post 34 in the vicinity of second end 38 thereof. Ball 40 may be reversibly attached to post 34. Means, 42, are provided for rigidly affixing second plate 28 to first plate 12 after second plate 28 has been received by first plate 12. As shown in FIG. 1, means 42 may include tab, 42, perpendicularly attached to front end, 44, of second plate 28, and having at least one hole, 46, adapted for permitting a screw body (not shown in FIG. 1) to pass therethrough such that the screw may be screwed into at least one threaded hole, 48, in front face 18 of plate 12 once plate 28 is slid into slot 22 of plate 12, thereby securing plate 28 to plate 12. Tab 42 may also include hole, 50, adapted for receiving a screw body therethrough effective for affixing plate 28 to the front side of the first vertebral body.

Surface 14 of plate 12 may have at least one longitudinal ridge, 52, protruding therefrom to assist in stabilizing plate 12 on the endplate of the first vertebral body. Surface 14 may also be roughened such that bone from the endplate may grow thereinto for further stabilization of plate 12 on the endplate.

Third flat plate, 54, adapted for attachment to the endplate of an opposing second vertebral body may have first flat surface, 56, second flat surface, 58, parallel thereto, front wall, 60, and rear wall, 62, slot, 64, opening through second flat surface 58 and at least through front wall 60, and means, 66, for attaching plate 54 to the second vertebral body. Beneficially, one example of slot 64 may have a dovetail cross section. One example of attaching means 66 is illustrated as tabs, 66*a* and 66*b*, having screw holes, 68*a* and 68*b*, therein for affixing plate 54 to the front side of the second vertebral body.

Fourth member, 70, having first flat surface, 72, second flat surface, 74, parallel thereto, front wall, 76, and rear wall, 78, first surface 72 being adapted to slide into slot 64 in third plate 54. Shown in FIG. 1 is that first flat surface 72 has a dovetail cross section, 80. Fourth member 70 also has slot, 82, therein opening through second flat surface 74 and through front wall 76 thereof, and first channel, 84, opening into slot 82 and also opening through front wall 76. First channel 84 is adapted to slidably and rotatably receive ball 40. Beneficially, channel 84 is circular in cross section, although other shapes may be envisioned. In what follows, hereinbelow, channels such as channel 84 may be oval or diamond-shaped, as examples. Means, 86, are provided for attaching fourth member 70 to the front of the second vertebral body, and is illustrated in FIG. 1 as a tab disposed perpendicularly to first surface 72, and having hole 88 therein adapted for permitting the body of a screw to pass therethrough and into the vertebral body. Means, 90, are provided for rigidly affixing fourth member 70 to third plate 54 after fourth member 70 has been received by the third plate, and are shown in FIG. 1 as at least one hole 90 adapted for permitting the body of a screw to pass therethrough and into at least one threaded hole, 92, in plate 54.

Fifth member, 94, having first flat surface, 96, second flat surface, 98, parallel thereto, front wall, 100, and rear wall, 102, is adapted to slide into slot 82 in fourth member 70, first surface 96 having second channel, 104, therein and opening through rear wall 102 and through second flat face 98. Second channel 104 is adapted to slidably and rotatably receive ball 40, while post 34 slidably fits through opening, 106, in second surface 98. Beneficially, channel 104 is circular in cross section, although other shapes may be envisioned. In what follows, hereinbelow, channels such as channel 104 may be oval or diamond-shaped, as examples. Means, 108, shown in FIG. 1 as flange 108 having at least one hole, 110, are provided for rigidly affixing fifth member 94 to fourth member 70, hole 110 being adapted such that the body of a screw may pass therethrough and into at least one matching threaded hole, 112, in fourth member 70. FIG. 1 shows the cross section, 114, of fifth member 94 as having a dove tail configuration to match slot 82 in fourth member 70. When fifth member 94 is inserted into fourth member 70, channel 104 in fifth member 94 and channel 84 in fourth member 70 form opposing, parallel channels wherein ball 40 may rotate and slide a chosen distance therein as determined by the length of opening 106 from the inside surface of wall, 116, in fourth member 70.

Surface 56 of plate 54 may have at least one longitudinal ridge, 118, protruding therefrom to assist in stabilizing plate 54 on the endplate of the second vertebral body. Surface 56 may also be roughened such that bone from the endplate may grow thereinto for further stabilization of plate 54 on the endplate.

Parallel, rotation limiting stubs, 120*a* and 120*b*, affixed to flange 108 of fifth member 94 and perpendicular to surface 98 thereof engage stub, 122, affixed to tab 42 of second plate 28 and perpendicular to surface 32 thereof, in such a manner that ball 40 is limited in the amount of rotation when capture in cooperating channels 84 and 104.

Components of artificial spinal implant 10, including screws, may be fabricated from non-ferromagnetic metals including titanium and titanium alloys in order to avoid interference with MRI investigations. Surfaces where metal-to-metal contact occurs, such as ball 40 in channels 84 and 104, may have metal surfaces coated with suitable polymers as is known in the medical arts, in order to avoid wear debris. The distance between surface 14 of plate 12 and surface 56 of plate 54 may be about 0.5 in. for cervical spinal implants, and about 1 in. for lumbar spinal implants for male adults, with correspondingly smaller implants for women and children.

It should be mentioned that other forms of attachment of the various components to one another may be envisioned. For example, the plates may be screwed together rather than requiring cooperating rectangular or dovetailing slots. Spring-loaded latches or spring devices utilizing rods or pins may be employed for attaching the plates, as examples, in place of screws. Further, although the plates and members hereof are illustrated as being rectangular in shape and having generally parallel surfaces, other shapes and orientations of the surfaces may be envisioned. Additionally, implant 10 hereof may also be utilized such that the plate attached to the upper spinal vertebra may be attached to the lower vertebra, and the implant effectively rotated by 180°.

Figure 2:
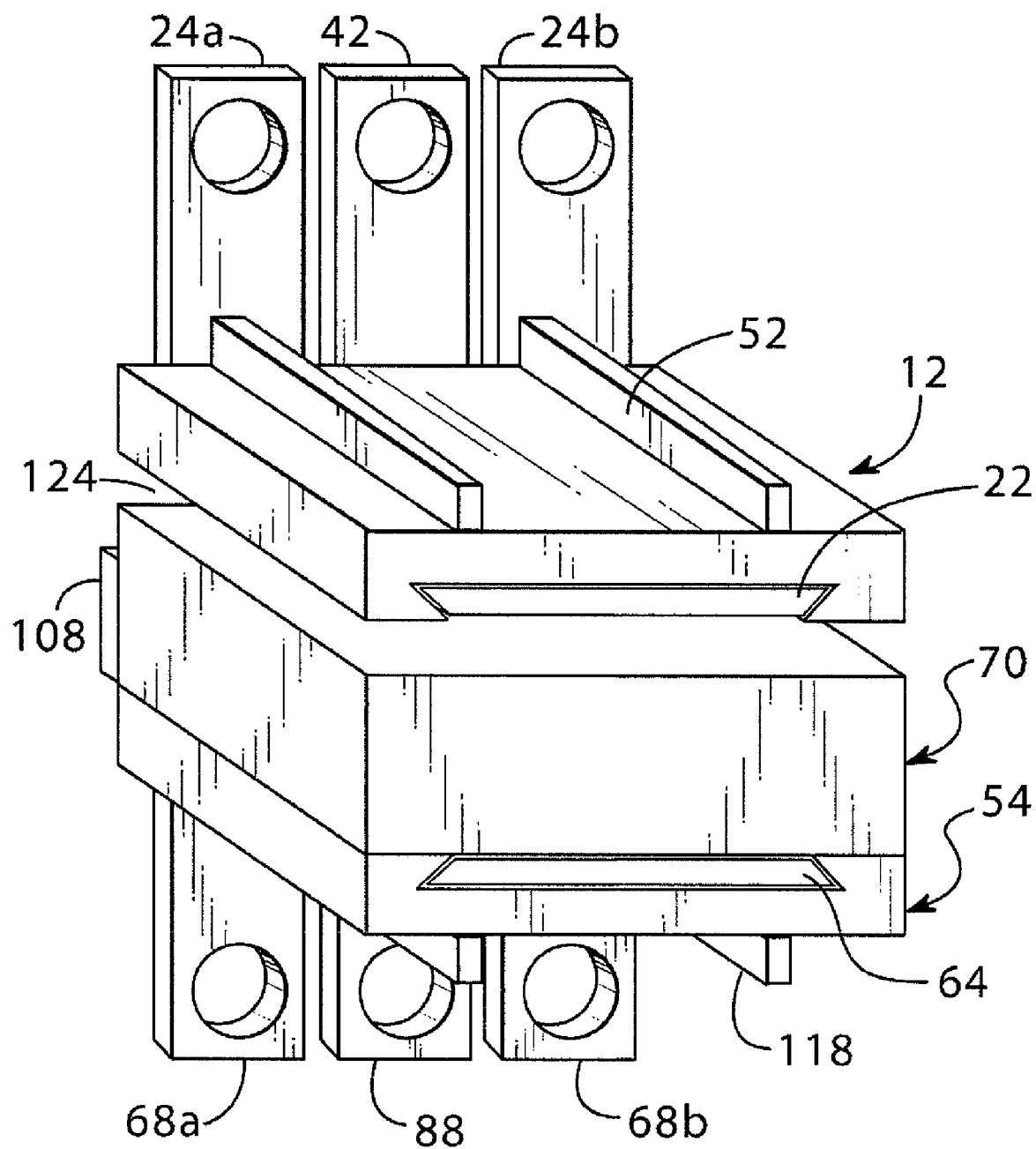
FIG. 2 is a schematic representation of a perspective assembled view of the embodiment of the artificial spine implant illustrated in FIG. 1 hereof.

FIG. 2 is a schematic representation of a perspective assembled view of the embodiment of the artificial spine implant illustrated in FIG. 1 hereof, clearly showing space, 124, between first plate 12 and fourth member 70 resulting from post 36 and ball 40 resting in cooperating channels 84 and 104.

Figure 3:
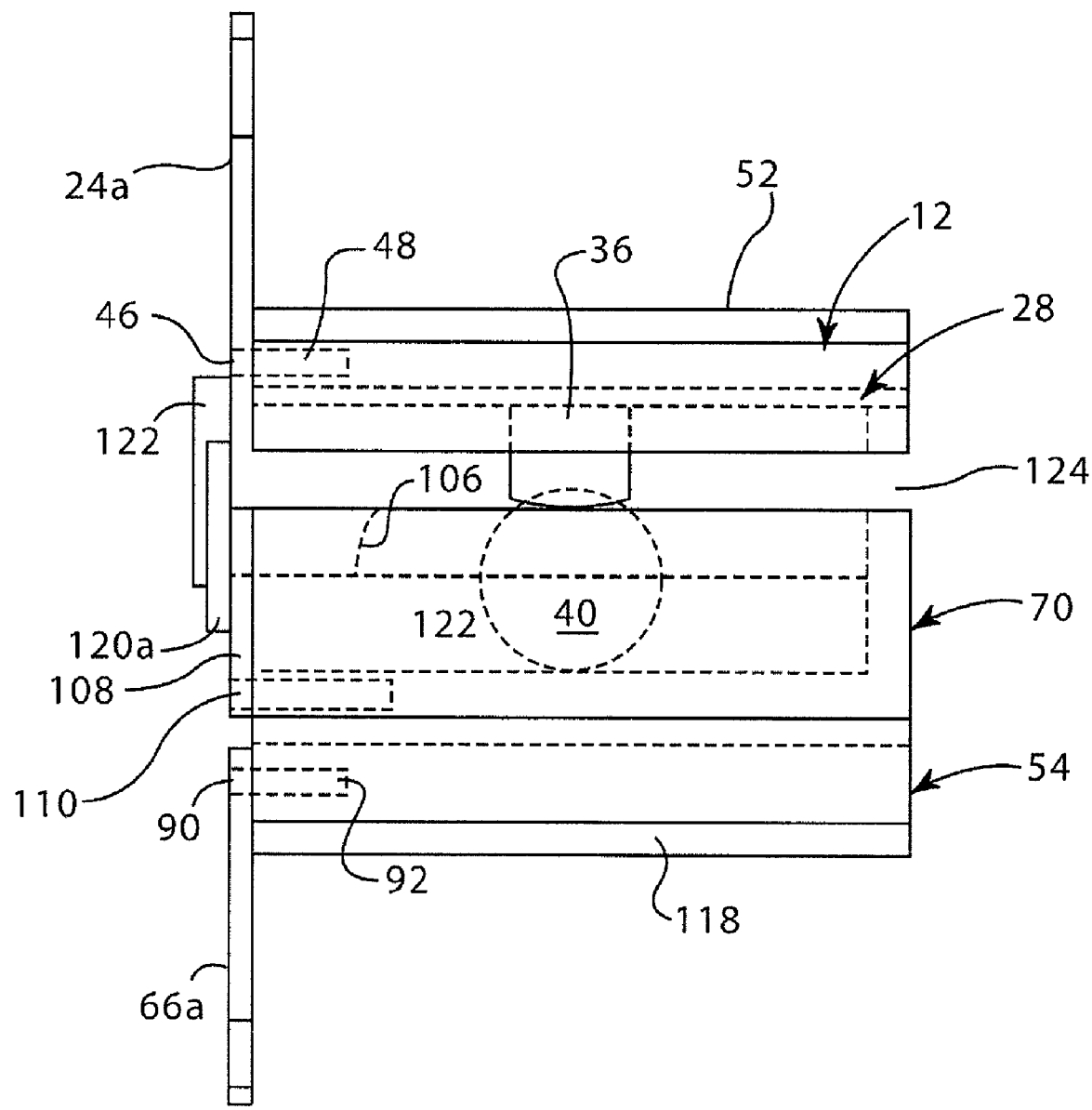
FIG. 3 is a schematic representation of a side view of the embodiment of the artificial spine implant illustrated in FIG. 1 hereof.

FIG. 3 is a schematic representation of a side view of the embodiment of the artificial spine implant illustrated in FIG. 1 hereof, illustrating the deployment of artificial spinal disk 10 between upper vertebral body, 126, and lower vertebral body, 128. It should be mentioned that artificial spinal disk 10 may also be mounted such that first plate 12 is in contact with lower vertebral body 128 and third plate 54 is in contact with upper vertebral body 126.

Figure 4:
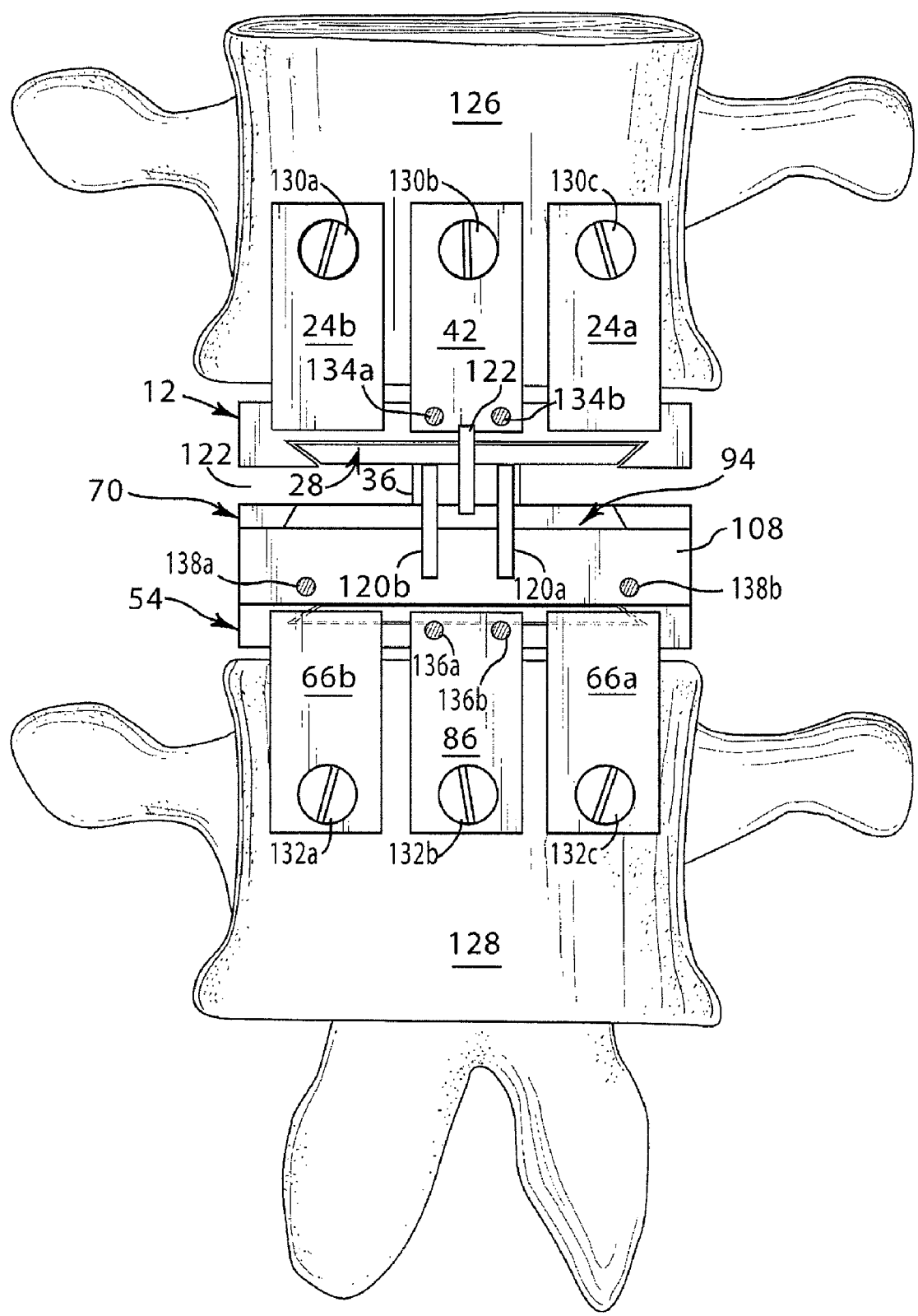
FIG. 4 is a schematic representation of the front view of the embodiment of the artificial spine implant illustrated in FIG. 1 hereof, showing the implant in place and attached to each of two opposing vertebral bodies.

FIG. 4 is a schematic representation of the front view of the embodiment of the artificial spine implant illustrated in FIG. 1 hereof, showing the implant in place and attached to each of two opposing vertebral bodies. Screws, 130*a*-130*c*, are shown as fastening plates 12 and 28 to upper vertebral body 126, while screws, 132*a*-132*c*, are shown fastening plate 54 and member 70 to lower vertebral body 128. Screws, 134*a* and 134*b,* fasten plate 28 to plate 12, screws, 136*a* and 136*b*, fasten member 70 to plate 54, and screws, 138*a* and 138*b,* attach member 94 to member 70.

Figure 5:
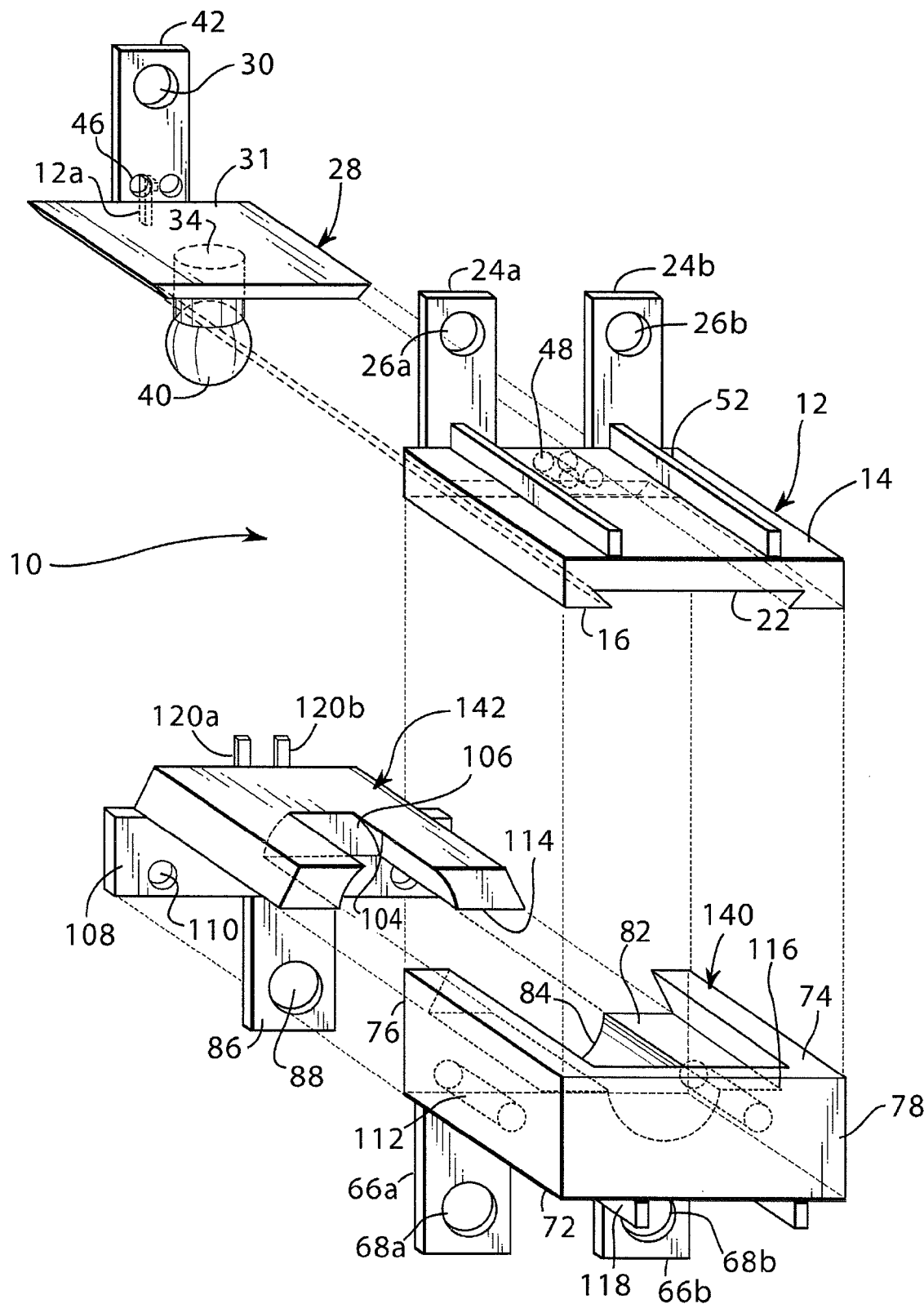
FIG. 5 is a schematic representation of an exploded perspective view of a four-piece embodiment of the artificial spinal disk hereof including a first flat plate effective for attachment to a first vertebral body; a second plate to which a post having a ball mounted thereon is attached, wherein the second plate may be reversibly received by the first plate; and two members when combined forming an enclosed channel for slidably and rotatably restraining the ball and post, one of the two members being attached to a second vertebral body opposing the first vertebral body.

FIG. 5 is a schematic representation of an exploded perspective view of another embodiment of the artificial spinal disk 10 hereof showing a four-piece version thereof, including first flat plate 12 effective for attachment to a first vertebral body; a second plate 28 to which post 34 having ball 40 mounted thereon is attached, wherein plate 28 is reversibly attached to plate 12, as described above; and two members, 140 and 142, which are similar to members 70 and 94, respectively, in FIG. 1 hereof, forming an enclosed channel for slidably and rotatably restraining ball 40, in a manner similar to that described above for members 70 and 94, member, 140, being attached to a second vertebral body opposing the first vertebral body.

Figure 6:
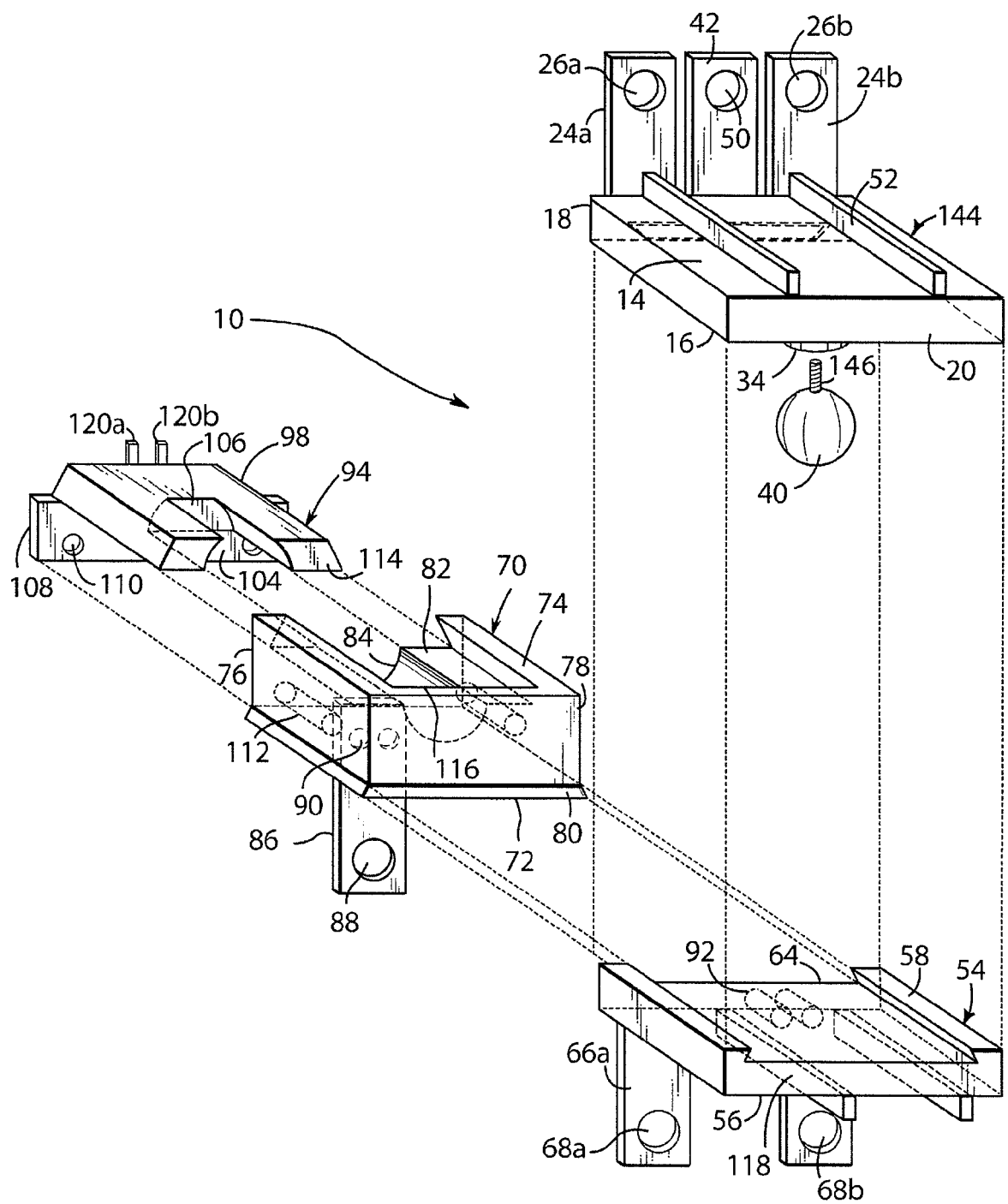
FIG. 6 is a schematic representation of an exploded perspective view of a second four-piece embodiment of the artificial spinal disk hereof including a first flat plate effective for attachment to a first vertebral body, and to which a post having a ball mounted thereon is attached; and two members when combined forming an enclosed channel for slidably and rotatably restraining the ball and post, the two members being reversibly attached to a third plate effective for attachment to a second vertebral body opposing the first vertebral body.

FIG. 6 is a schematic representation of an exploded perspective view of a second, four-piece embodiment of the artificial spinal disk 10 hereof, including first flat plate, 144, effective for attachment to a first vertebral body, and to which post 34 having ball 40 mounted thereon is attached in a similar manner to plates 12 and 28 in FIG. 1 hereof when combined as described hereinabove; and two members 70 and 94 when combined forming an enclosed channel for slidably and rotatably restraining ball 40 and post 34, members 70 and 94 being reversibly attached to second plate 54 effective for attachment to a second vertebral body opposing the first vertebral body, as also described hereinabove. Ball 40 may be reversibly attached to post 34 using threaded member, 146, which is adapted to be screwed into a threaded hole in ball 40 (not shown in FIG. 6).

Figure 7:
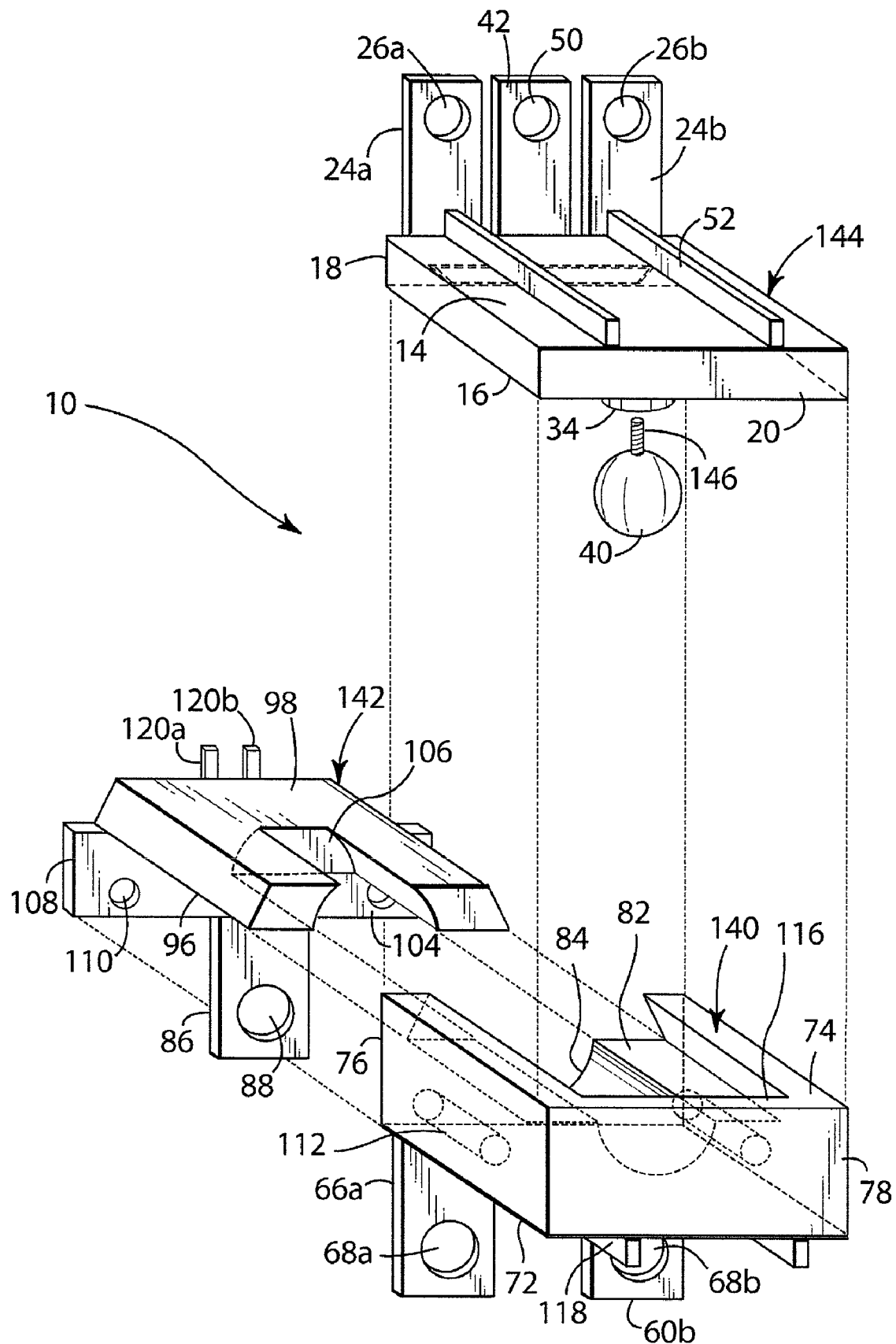
FIG. 7 is a schematic representation of an exploded perspective view of a three-piece embodiment of the artificial spinal disk hereof including a first flat plate effective for attachment to a first vertebral body and to which a post having a ball mounted thereon is attached; and two members when combined forming an enclosed channel for slidably and rotatably restraining the ball and post, one of the two members being attached to a second vertebral body opposing the first vertebral body.

FIG. 7 is a schematic representation of an exploded perspective view of a three-piece embodiment of the artificial spinal disk 10 hereof including first flat plate 144 effective for attachment to a first vertebral body and to which post 34 having ball 40 mounted thereon is attached in a similar manner to plates 12 and 28 in FIG. 1 hereof when combined as described hereinabove; and two members, 140 and 142, which are similar to members 70 and 94, respectively, in FIG. 1 hereof, forming an enclosed channel for slidably and rotatably restraining ball 40 and post 34, in a manner similar to that described above for members 70 and 94, member, 140, being attached to a second vertebral body opposing the first vertebral body. As stated above, ball 40 may be reversibly attached to post 34 using threaded member, 146, which is adapted to be screwed into a threaded hole in ball 40 (not shown in FIG. 7).

Figure 8A:
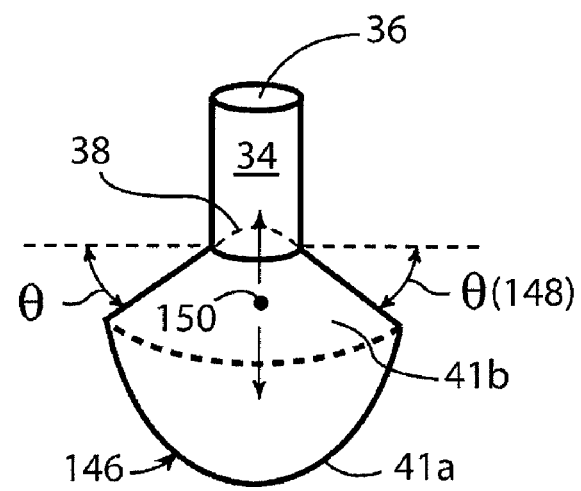

FIG. 8A is a schematic representation of another embodiment, 146, of ball 40 mounted using post 34 to second flat plate 28 and illustrated in FIG. 1, hereof, wherein spherical portion, 41a, of ball 40 is transitioned into conical portion, 41b, the smaller end of the conical portion being attached to post 34 at wall 38. Angle, θ (148), formed between the wall of conical portion 41b and a line parallel to wall 38 of post 34, may be chosen to determine the forward and rearward flexing of assembled disk 10. Adjustment of angle θ may be achieved by moving center, 150, of spherical portion 41a towards or away from wall 38. Angles, θ, between 10° and 30° are anticipated to be useful, although other angles may be used.

Figure 8B:
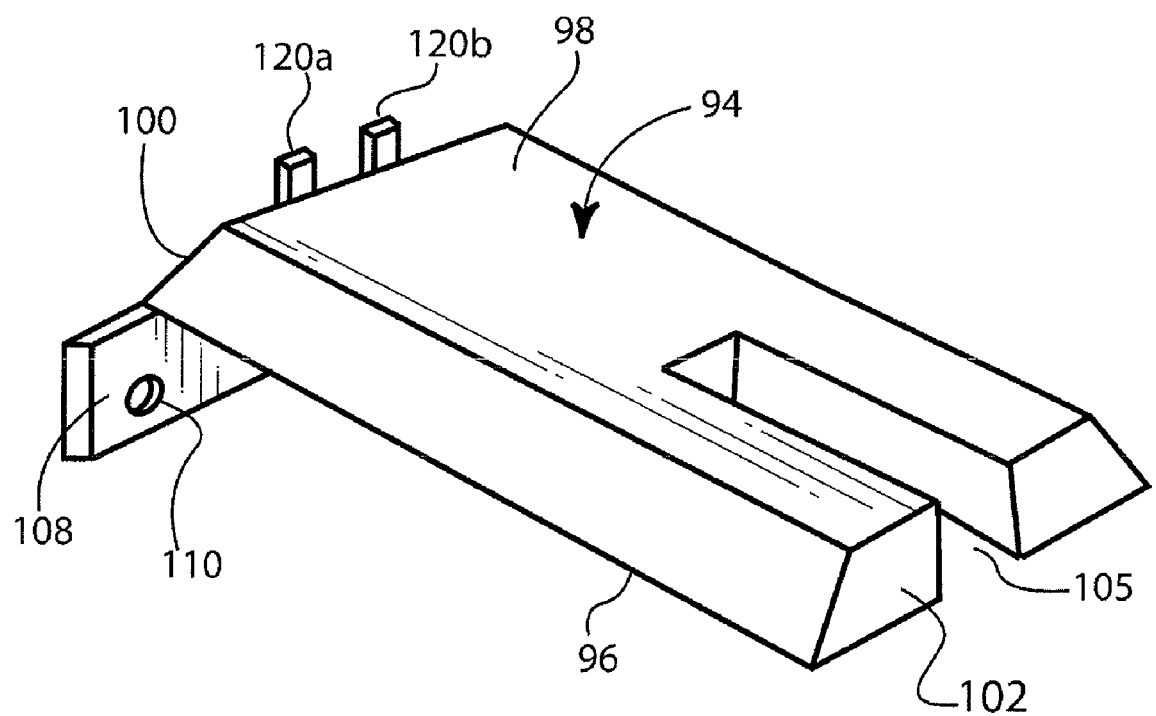
FIG. 8B is a schematic representation of one of the two members combined to form a channel for slidably and rotatably restraining the ball and post, adapted to receive the embodiment of the ball described in FIG. 8A hereof.

FIG. 8B is a schematic representation of fifth member 94 adapted to receive and cooperate with the embodiment of the ball described in FIG. 8A hereof. Fifth member 94, described hereinabove, may have first flat surface 96 second flat surface 98 parallel thereto, front wall 100 and rear wall 102, and is adapted to slide into slot 82 in fourth member 70. Slot, 105, opening through rear wall 102 and through first flat face 96 and second flat face 98, is adapted to slidably and rotatably receive post 34. Slot 105 may have a rectangular cross section. When cooperating with first channel 84 in fourth member 70, slot 105 permits ball 146 to slidably and rotatably move in the channel formed thereby and permit forward, rearward and lateral flexing movement for disk 10. Rounding the rectangular edges of slot 105 may assist in the movement of ball 146 therein.

The employment of ball 146 shown in FIG. 8A hereof with the embodiment of fifth member 94 shown in FIG. 8B hereof, may reduce the height of the combination of the post, the ball, and the assembly of the fourth and fifth members illustrated in FIG. 1 hereof by about 50%, while maintaining effective articulation of disk 10. It should be mentioned that this embodiment of ball 146 and fifth member 94 may be applied to the embodiments of the present invention illustrated in FIGS. 5, 6, and 7 hereof, except that the changes to fifth member 94 described hereinabove are applied to member 142 in FIGS. 5 and 7, hereof.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An artificial spinal disk for placement between adjacent spinal vertebrae to replace disk material, comprising in combination:
   a first flat plate for attaching to the endplate of a first vertebral body said first flat plate having a first surface and an opposing second surface, a front wall, and a slot opening through the second surface and through the front wall;
   a second flat plate having a first surface and an opposing second surface, adapted to slide into the slot in said first plate;
   a post having a first end, and a second end perpendicularly attached to the second surface of said second plate and extending through the slot opening in the second surface of said first plate;
   a ball having a portion of the spherical surface thereof transitioned into a conical portion, wherein the smaller end of the conical portion is mounted on the first end of said post;
   means for rigidly affixing said second plate to said first plate;
   a third flat plate for attaching to the endplate of a second vertebral body the endplate of the second vertebral body opposing the endplate of the first vertebral body, said third flat plate having a first surface and an opposing second surface, a front wall, and a slot opening through the second surface and through the front wall;
   a fourth member having a first surface, an opposing second surface, a front wall, and adapted to slide into the slot in said third plate, said fourth member having a slot therein opening through the second surface and through the front wall thereof and a first channel within the slot opening through the front wall of said fourth member adapted to slidably and rotatably receive said ball;
   means for rigidly affixing said fourth member to said third plate;
   a fifth member having a first surface, an opposing second surface, and a rear wall, and adapted to slide into the slot in said fourth member, the second surface having a second channel therein adapted to slidably and rotatably receive said ball and said post, and opening through the rear wall; and
   means for rigidly affixing said fifth member to said fourth member, whereby the channel in said fifth member and the channel in said fourth member form opposing, parallel channels wherein said ball may rotate and slide a chosen distance therein.

2. The disk of claim 1, wherein the first channel and the second channel are semi-cylindrical.

3. The disk of claim 1, further comprising means for attaching said first flat plate to the side of the endplate of the first vertebral body; and means for attaching said third flat plate to the side of the endplate of the second vertebral body.

4. The disk of claim 1, wherein said second plate has a dove-tail shaped cross section, and the slot in said first plate has a corresponding shape adapted to slidably receive said second plate; the fifth member has a dove-tail shaped cross section and the slot in said fourth member has a corresponding shape adapted to slidably receive said fifth member; and the first flat surface of said fourth member has a dove-tail cross section and the slot in said third plate has a corresponding shape adapted to slidably receive said fourth member.

5. The disk of claim 1, wherein means are provided for detachably attaching said ball to said post.

6. The disk of claim 1, wherein the first surface of said first flat plate and the first surface of said third flat plate are roughened.

7. The disk of claim 1, wherein the first surface of said first flat plate and the first surface of said third flat plate have longitudinal ribs.

8. The disk of claim 1, wherein means are provided to prevent over-rotation of said ball in the opposing, parallel channel formed by the channel in said fifth member and the channel in said fourth member.

9. The disk of claim 1, further comprising means for attaching said second plate to the side of the first vertebral body, and means for attaching said fourth body to the side of said second vertebral body.

10. An artificial spinal disk for placement between adjacent spinal vertebrae to replace disk material, comprising in combination:
   a first flat plate for attaching to the endplate of a first vertebral body said first flat plate having a first surface and an opposing second surface, a front wall, a slot opening through the second flat surface and through the front wall;
   a second flat plate having a first surface and an opposing second flat surface, adapted to slide into the slot in said first plate;
   a post having a first end, and a second end perpendicularly attached to the second surface of said second plate and extending through the slot opening in the second surface of said first plate;
   a ball having a portion of the spherical surface thereof transitioned into a conical portion, wherein the smaller end of the conical portion is mounted on the first end of said post;
   means for rigidly affixing said second plate to said first plate;
   a third member having a first surface, an opposing second surface, a front wall, the first flat surface adapted to be attached to the endplate of a second vertebral body opposing the endplate of the first vertebral body, said third member having a slot therein opening through the second surface and through the front wall thereof and a first channel within the slot opening through the front wall of said third member adapted to slidably and rotatably receive said ball;
   a fourth member having a first surface, a second surface parallel thereto, and a rear end, and adapted to slide into the slot in said third member, the second surface having a second channel therein adapted to slidably and rotatably receive said ball, and opening through the rear wall; and
   means for rigidly affixing said fourth member to said fifth member, whereby the channel in said third member and the channel in said fourth member form opposing, parallel channels wherein said ball may rotate and slide a chosen distance therein.

11. The disk of claim 10, wherein the first channel and the second channel are semi-cylindrical.

12. The disk of claim 10, further comprising means for attaching said first flat plate to the front side of the endplate of the first vertebral body; and means for attaching said third member to the front side of the endplate of the second vertebral body.

13. The disk of claim 10, wherein means are provided for detachably attaching said ball to said post.

14. The disk of claim 10, wherein the first surface of said first plate and the first flat surface of said third flat plate are roughened, and have longitudinal ribs.

15. An artificial spinal disk for placement between adjacent spinal vertebrae to replace disk material, comprising in combination:
   a first flat plate for attaching to the endplate of a first vertebral body said first flat plate having a first surface and an opposing second surface;
   a post having a first end, and a second end perpendicularly attached to the second surface of said first plate;
   a ball having aportion of the spherical surface thereof transitioned into a conical portion, wherein the smaller end of the conical portion is mounted on the first end of said post;
   a second flat plate for attaching to the endplate of a second vertebral body the endplate of the second vertebral body opposing the endplate of the first vertebral body, said second flat plate having a first surface and an opposing second surface parallel thereto, a front wall, and a slot opening through the second surface and through the front wall;
   a third member having a first surface, an opposing second surface and a front wall, and adapted to slide into the slot in said second plate, said third member having a slot therein opening through the second surface and through the front wall thereof and a first channel within the slot opening through the front wall of said third member adapted to slidably and rotatably receive said ball;
   means for rigidly affixing said third member to said second plate;
   a fourth member having a first surface, an opposing second flat surface and a rear wall, and adapted to slide into the slot in said third member, the second surface having a second channel therein adapted to slidably and rotatably receive said ball, and opening through the rear wall; and
   means for rigidly affixing said fourth member to said third member, whereby the channel in said third member and the channel in said fourth member are opposing, parallel channels, wherein said ball may rotate and slide a chosen distance therein.

16. The disk of claim 15, wherein the first channel and the second channel are semi-cylindrical.

17. The disk of claim 15, further comprising means for attaching said first flat plate to the front side of the endplate of the first vertebral body; and means for attaching said second member to the front side of the endplate of the second vertebral body.

18. The disk of claim 15, wherein means are provided for detachably attaching said ball to said post.

19. The disk of claim 15, wherein the first surface of said first flat plate and the first surface of said second flat plate are roughened, and have longitudinal ribs.

20. An artificial spinal disk for placement between adjacent spinal vertebrae to replace disk material, comprising in combination:
   a first flat plate for attaching to the endplate of a first vertebral body said first flat plate having a first surface and an opposing second surface;
   a post having a first end, and a second end perpendicularly attached to the second surface of said first plate;
   a ball having a portion of the spherical surface thereof transitioned into a conical portion, wherein the smaller end of the conical portion is mounted on the first end of said post;
   a second member having a first surface, an opposing second surface, and a front wall, the first surface adapted to be attached to the endplate of a second vertebral body opposing the endplate of the first vertebral body, said second member having a slot therein opening through the second surface and through the front wall thereof and a first channel within the slot opening through the front wall of said second member adapted to slidably and rotatably receive said ball;

a third member having a first surface, an opposing second surface and a rear wall, and adapted to slide into the slot in said second member, the second surface having a second channel therein adapted to slidably and rotatably receive said ball, and opening through the rear wall; and means for rigidly affixing said third member to said second member, whereby the channel in said second member and the channel in said third member form opposing, parallel channels wherein said ball may rotate and slide a chosen distance therein.

21. The disk of claim 20, wherein the first channel and the second channel are semi-cylindrical.

22. The disk of claim 20, further comprising means for attaching said first flat plate to the front side of the endplate of the first vertebral body; and means for attaching said second member to the front side of the endplate of the second vertebral body.

23. The disk of claim 20, wherein means are provided for detachably attaching said ball to said post.

24. The disk of claim 20, wherein the first surface of said first flat plate and the first surface of said second member are roughened, and have longitudinal ribs.

* * * * *